(12) United States Patent
Link et al.

(10) Patent No.: US 7,947,465 B2
(45) Date of Patent: *May 24, 2011

(54) SIMULTANEOUS ASSAY FOR DETERMINING DRUGS

(75) Inventors: William F. Link, El Cerrito, CA (US); Renato B. del Rosario, Benicia, CA (US); Randy V. Sweet, Pinole, CA (US); David L. King, Benicia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 12/187,661

(22) Filed: Aug. 7, 2008

(65) Prior Publication Data

US 2009/0053733 A1    Feb. 26, 2009

Related U.S. Application Data

(63) Continuation-in-part of application No. 11/841,649, filed on Aug. 20, 2007, now abandoned.

(51) Int. Cl.
*G01N 33/00* (2006.01)
(52) U.S. Cl. ............ 435/7.93; 435/7.1; 435/287.2; 436/513; 436/517; 436/518; 436/523; 436/526; 436/538; 436/540; 436/10; 436/18; 436/172; 436/175; 422/73; 422/82.08; 422/82.09; 424/9.2
(58) Field of Classification Search .......... 435/6, 7.1, 435/7.93, 287.2; 436/513, 517, 518, 523, 436/526, 538, 540, 10, 18, 172, 175, 177; 422/73, 82.08, 82.09, 101; 424/9.2
See application file for complete search history.

(56) References Cited

U.S. PATENT DOCUMENTS 5,525,524 A    6/1996    Buechler et al.
(Continued)

FOREIGN PATENT DOCUMENTS

WO    WO 01/79844 A1    10/2001

OTHER PUBLICATIONS

Link, W. et al.; "Development of a Multiplex Toxicology Panel of Immunoassay"; 2006, *The International Association of Forensic Toxicologists, 44th International Meeting*, pp. 1-2.

(Continued)

*Primary Examiner* — Gailene R Gabel
(74) *Attorney, Agent, or Firm* — Kilpatrick, Townsend and Stockton LLP.; M. Henry Heines (57) ABSTRACT

Bodily fluid is analyzed for the presence of drugs of a selected panel of drugs in a simultaneous assay in which sample of the fluid is incubated with additional amounts of all drugs of the panel, antibodies specific to each of the drugs of the panel, and microparticles, the microparticles being divided into subsets, one subset for each drug in the panel and each subset distinguishable from the others. The incubation is performed in a liquid medium in which competitive binding occurs, the drugs in the sample competing with those added to the assay medium for binding to the antibodies. In one procedure, the added drugs are pre-coupled to the microparticles while the antibodies are not, and the incubation is followed by further incubating the microparticles with labeled ligands that have affinity for the antibodies. In an alternative procedure, the added drugs are not coupled to the microparticles but are pre-labeled, while the antibodies are pre-coupled to the microparticles, and the assay proceeds without further incubation. In both alternatives, the microparticles are ultimately recovered from the assay medium and from any unbound species, and the recovered microparticles are analyzed by flow cytometry to obtain indications of the presence of the various drugs in the sample in an inverse manner by detection of the label, each drug differentiable from the others by the distinguishing features of the microparticles.

18 Claims, 5 Drawing Sheets

U.S. PATENT DOCUMENTS

| | | | |
|---|---|---|---|
| 5,851,776 A | 12/1998 | Valkirs | |
| 6,777,190 B1 | 8/2004 | Anderson et al. | |
| 7,141,431 B2 * | 11/2006 | Chandler et al. | 436/166 |
| 7,560,239 B2 * | 7/2009 | Lin et al. | 435/7.1 |
| 7,608,465 B2 * | 10/2009 | Watkins et al. | 436/500 |
| 2004/0126904 A1 | 7/2004 | Watkins et al. | |
| 2006/0099664 A1 | 5/2006 | Ullman et al. | |
| 2009/0053832 A1 * | 2/2009 | Link et al. | 436/537 |

OTHER PUBLICATIONS

Pirnay, S.O. et al.; "Sensitive Gas Chromatography-Mass Spectrometry Method for Simultaneous Measurement of MDEA, MDMA and Metabolites HMA, MDA and HMMA in Human Urine"; 2006, *Clinicla Chemistry,* vol. 52, No. 9, pp. 1728-1734.

* cited by examiner

SIMULTANEOUS ASSAY FOR DETERMINING DRUGS

CROSS-REFERENCE TO RELATED APPLICATIONS

This is a continuation-in-part of application Ser. No. 11/841,649 filed Aug. 20, 2007, the entire contents of which are hereby incorporated herein.

BACKGROUND OF THE INVENTION AND PRIOR ART

This invention relates to multiplex assays for simultaneous detection of the presence and optionally semi-quantization of drugs in a sample, for instance a sample of a human or other (non-human) mammalian body fluid, or of the body fluid of a non-mammalian vertebrate. By "drugs" we mean to include narcotics, prescription drugs, over-the-counter medicines, and their metabolites. The invention includes both methods of conducting such assays and kits for use in such methods. As used herein, the term "drug" or "drugs" is meant to include the active substances, derivatives of those substances, for instance salts or esters, and metabolites of either the drugs or their derivatives.

Determination of drugs in a sample of a bodily fluid, particularly a human or mammalian fluid sample, is needed in several different situations. In a law-enforcement environment it may be necessary to ascertain whether a suspect or a victim has taken one or more narcotics or other drugs that may be abused. Similarly in health situations such as hospital emergency rooms and other hospital units or in a drug treatment program it may be necessary to determine whether a patient has taken one or more of such drugs. In both situations the person whose body fluid is being tested may not be in a condition to provide information about drugs that have been taken, or may be lying, or absent, or deceased. If the patient is an animal, again there may be no-one present to provide information about drugs that may have been administered.

In such situations it is common to run a series of discrete tests for individual drugs and/or their metabolites, each test requiring its own set of reagents, controls and calibrators. However, it would be far more convenient, and would consume significantly less time in running the test (and time could be critical in some cases), to have a multiplex assay, in which a number of assays could be run simultaneously, and a single or combined result produced.

Multiplex assays have been developed for a number of applications. A known problem, however, in designing such assays is the potential for what is known as "cross-talk", i.e. the potential for a particular antibody to bind to a plurality of drug conjugates, especially conjugates containing related drugs such as amphetamine and methamphetamine. Such problem is discussed, for example, in U.S. Pat. No. 5,525,524, whose inventors proposed the solution of including a crosstalk inhibitor in the assay.

Test procedures for simultaneously assaying for the presence of two or more drugs are described in U.S. Pat. Nos. 5,851,776 of Valkirs and 6,777,190 of Buechler et al. These all relate to lateral-flow chromatographic assays on a membrane or other porous or non-porous material. At least two products of this type are currently available commercially: the Triage® drugs-of-abuse panel from Biosite Incorporated (San Diego, Calif., USA) and the TOX-See™ drug screen test from Bio-Rad Laboratories, Inc. (Hercules, Calif., USA). However, these assays are not optimal for larger-scale automated testing and are only qualitative, not semi-quantitative, assays. U.S. published application 2006/99664 of Ullman et al. describes a multiplex assay for detection of drugs, but the example is qualitative and involves only two drugs.

BRIEF SUMMARY OF THE INVENTION

In one aspect this invention comprises a method for assaying a sample of a human or mammalian bodily fluid to simultaneously determine whether one or more of a plurality of drugs and/or metabolites thereof are present in said sample and optionally to perform a semi-quantitative assay for said drug or drugs, comprising:

(a) incubating the sample in a competitive assay with a plurality of drug conjugates and a plurality of primary antibodies that bind to the drugs whose presence and optionally whose amount is to be determined, wherein either the plurality of drug conjugates or the plurality of primary antibodies is coupled to microparticles comprising magnetically responsive material, the particles being divided into subsets of particles, each distinguishable from the others by one or more differentiation parameters and by the drug to which they are coupled;

(b) incubating the product of step (a) with a liquid medium comprising one or more labeled ligands for the primary antibodies or the drug conjugates;

(c) magnetically separating microparticles in all of said groups from said liquid medium; and defining said liquid medium as a first liquid medium;

(d) resuspending said microparticles separated therefrom in a second liquid medium; and (e) analyzing said microparticles in said second liquid medium by flow cytometry and identifying drugs present in the sample, and optionally calculating a semi-quantitative result for drugs found to be present;

provided that step (b) is not conducted in the method if a drug conjugate is used in step (a) that is detectable via a label incorporated in the species to which the drug or drug derivative is conjugated.

In another aspect the invention comprises a kit for carrying out the above process comprising (a) a plurality of conjugates of drugs whose presence and optionally semi-quantitative amount is to be determined; (b) a plurality of primary drug antibodies that bind to the drugs to be determined; (c) a series of magnetically responsive particles coupled either to said plurality of drugs or to said plurality of primary antibodies, the particles being divided into subsets of particles, each distinguishable from the others by one or more differentiation parameters and by the substance to which they are coupled; and (d) a labeling reagent comprising one or more labeled ligands that bind to the said primary drug antibodies or drug conjugates.

DETAILED DESCRIPTION OF THE INVENTION

The assay of the present invention combines the concept of competitive immunological binding with the concept of multiplex analytical techniques, for a preselected panel of drugs. With these combined concepts, a sample of bodily fluid is analyzed in accordance with the invention for all drugs in the panel in a single analysis. In accordance with known competitive binding protocols, the competitive binding in the present invention places each drug that may be present in the sample in direct competition with an added amount of the same drug for a limited number of antibody binding sites on antibodies that have specific binding affinity for the drug. The added amount of the drug differs from the drug in the sample in one of two ways: the added drug is either coupled to microparticles or coupled to a label. In cases where the added drug is coupled to microparticles, the antibodies are neither coupled to microparticles nor labeled, and the microparticle-bound drug competes with the drug in the sample for the antibody binding sites. In cases where the added drug is coupled to a label, the antibodies are coupled to microparticles, and labeled drug competes with the drug in the sample for the microparticle-bound antibodies. Since the added drug in these latter cases is already labeled, identification of the microparticles that have acquired a label can proceed directly. In the former case (where neither the added drug nor the microparticles are labeled), label is introduced by a second incubation in which the assay medium is incubated with labeled anti-IgG antibodies which will bind to all antibodies present in the medium, and identification of the microparticles that have acquired a label proceeds after this second incubation. In both cases, identification of the microparticles that have acquired a label is achieved by first recovering the microparticles from the assay medium, so that only those labels that have become bound to the microparticles are detected. In both cases as well, the result is an inverse indication of the presence of the drug in the sample, i.e., the greater the amount of label detected on the microparticles, the less the amount of that drug in the original sample.

The multiplex aspect of the invention resides in the use of microparticles that are divided into subsets, with one subset for each drug of the panel, and each subset distinguishable from the others by one or more differentiation parameters. In cases where the added drugs are coupled to microparticles, a separate drug is coupled to each subset of microparticles. In cases where the added drugs are labeled and not coupled to microparticles while the antibodies are coupled to the microparticles, each subset of microparticles contains only antibodies that are specific for a single drug. Thus, the competitive binding reactions described above occur on a separate subset of microparticles for each drug in the panel. The differentiation parameters permit the various subsets to be detected independently and yet all in a single analytical procedure.

In another aspect the invention comprises a kit for carrying out the above process comprising (a) a plurality of conjugates of drugs whose presence and optionally semi-quantitative amount is to be determined; (b) a plurality of primary drug antibodies that bind to the drugs to be determined; (c) a series of magnetically responsive particles coupled either to said plurality of drugs or to said plurality of primary antibodies, the particles being divided into subsets of particles, each distinguishable from the others by one or more differentiation parameters and by the substance to which they are coupled; and (d) a labeling reagent comprising one or more labeled ligands that bind to the said primary drug antibodies or drug conjugates.

In the first step of the process, the sample (typically from about 2 to about 15 µL) is contacted or incubated in a competitive assay with from about 10 to about 100 µL of beads or microparticles as described below and comprising magnetically responsive material having either a plurality of drugs or a plurality of antibodies for those drugs coupled to the microparticles, and from about 10 to about 100 µL of a liquid reagent containing either a plurality of antibodies (hereinafter "primary antibodies") that bind to the drugs whose presence is to be determined, and for which a semi-quantitative determination may also be made, or a plurality of drugs that are to be determined, conjugated, for instance, to proteins. The drugs or primary antibodies may be coupled directly to the microparticles, for instance through covalent binding with functional groups of compounds coated on the microparticles. Preferably, however, they are indirectly coupled to the microparticles through proteins, nucleotide sequences, peptides, amino acids and the like. If the reagent contains the primary antibodies, then the concentration of primary antibodies in that reagent is important for a good analysis, and in general is from about 0.01 to about 20 µg/mL, preferably from about 0.1 to about 10 µg/mL. Incubation conditions are from about 15 to about 45° C. and from about 2 to about 8 minutes. Any drugs or drug metabolites in the sample will compete for a limited number of antibody binding sites with drugs or metabolites provided in the kits.

The primary antibodies are selected for use in the process and kits based on possession of the specificity characteristics that are also required for single-analyte tests. They must be free of significant cross-reactivity with unrelated drugs and with related compounds whose presence in specimens is not diagnostically meaningful, and, in many cases, the assay must cross-react with a variety of related compounds. For example, a test for opiates may be based on one antibody that is able to detect morphine, codeine, hydrocodone and perhaps other opiate drugs of medical importance. However, the assay cannot cross-react significantly with certain opiates, such as dextromethorphine, which are found in non-prescription cough medicine. Additionally, an acceptable antibody for an opiates assay must not cross-react with unrelated drugs, including other drugs that are detected by other assays within the multiplex panel. The same selection criteria apply whether the drug antibodies are used in an assay design where the antibodies are presented in liquid phase, or if the drug antibodies are attached to a solid phase such as magnetic microparticles and the drug conjugates are contained in the reagent.

In addition to these criteria, the assays of this invention also require antibodies and drug derivatives (attached to microparticles in the panel) that avoid "cross-talk", i.e. antibody binding to an inappropriate drug-protein conjugate whether the conjugate is coated on the microparticle's surface or is in solution. In selecting antibodies for use in the process and kits of the present invention, therefore, some testing may be needed to ascertain which of various available antibodies will provide optimum results in terms of having relatively little cross-reactivity with unrelated drugs or cross-talk with unrelated microparticles or microparticle conjugates, while still being reactive with related compounds whose presence and/or amount is to be determined. The tests by which such antibodies are judged for use in the present invention are described in the examples below.

The total products of the first incubation step can be then further incubated, as described below, without separation of any materials. However, preferably unbound materials are separated from the microparticles with their bound materials before the process is continued. This separation can be carried out by magnetically separating the microparticles from the reaction medium, aspirating the reaction medium, adding wash buffer, and aspirating the wash buffer. Alternatively, instead of separation, the wash buffer is not added and the assay proceeds directly to the addition of labeled anti-IgG or other labeled ligand. Either the total product from step (a) or the group of washed particles is then incubated for a period of from about 2 to about 10 minutes at from about 15 to about 45° C., preferably from about 32 to about 40° C. with from about 20 to about 200 µL of a reagent containing one or more labeled ligands for the primary antibodies. Preferably the one or more ligands are one or more anti-IgG antibodies. Other possible ligands include protein A, protein G and streptavidin. The preferred label for the ligands is a fluorescent label, most preferably phycoerythrin. However, other typical labels such as biotin, enzymes, rhodamine or radioactive isotopes may be used. In a preferred embodiment the ligand is a "universal" reporter, most preferably a labeled secondary antibody or other ligand that will bind to all of the primary drug antibodies bound to the drug derivative on the solid phase. In general, the amount of secondary antibodies or other ligands is the appropriate amount for carrying out such assays; however, in a preferred embodiment this reagent also will contain an excess of either labeled or unlabeled secondary antibodies, most preferably unlabeled anti-IgG antibodies. The system allows for using primary antibodies from more than one species by adding additional antibody of appropriate specificity. For example, an assay using primary antibodies derived from mice may require anti-mouse IgG antibody labeled with phycoerythrin or another label. An assay using antibodies derived from mice for some drugs and from sheep for others may require a second secondary antibody, for instance, anti-sheep-IgG antibody labeled with phycoerythrin or another suitable label, in addition to labeled anti-mouse IgG. In the present case the system includes anti-mouse to tag the mouse monoclonals and anti-sheep to tag sheep polyclonals. Cross-reactivity of the anti-sheep with mouse antibodies (and vice versa) is benign. Preferably, interaction of anti-mouse and anti-sheep antibodies is minimized by obtaining both from the same species (donkey, for example).

The secondary antibodies are present in the reagent in excess or near excess, preferably from about 90 to about 500, most preferably in from about 95 to about 200 percent excess, with respect to signal generation. In other words, concentration of secondary antibody should be such that diluting it by 10 to 20% or more will not appreciably reduce the signal generated by the immunoassays in the multiplex panel. For a given assay, the amount of excess secondary antibody is initially determined empirically, using different dilutions and excesses, until a further 10-50% dilution of the reagent does not change the signal. Once the appropriate excess quantity is determined for a given assay, the secondary antibody reagent can be made up and included in the kits The excess secondary antibody can be prepared by using large amounts of labeled antibody, or, preferably, by mixing labeled and unlabeled antibody. If unlabeled antibody is used to provide the excess concentration of secondary antibody, the amounts of labeled and unlabeled antibody can be easily adjusted so that the appropriate level of signal is obtained and the total amounts of anti-mouse and anti-sheep are in excess concentrations. Formulating this reagent with excess amounts of secondary antibody improves assay precision by reducing the effect of pipetting error when the reagent is added to the reaction, and reducing the dilution effect that may occur if wash buffer remains after the wash steps that follow the first incubation. Formulation with excess antibody reaches a saturation level of binding very quickly, allowing a short incubation of 180 seconds that produces a constant level of signal if the incubation is varied by 20 seconds or more, for instance. This attribute improves precision of the assay by greatly reducing the effect of variation in timing of the second incubation. The improvements to precision mentioned above apply to both manual and automated assays.

When both labeled and unlabeled antibodies are contained in this reagent, the ratio of unlabeled to labeled anti-antibody is from about 2:1 to about 20:1, depending on the avidity of the antibody, the degree to which the antibody is labeled, and the concentrations required for the given assay. The ratio is determined empirically; in one case the ratio of unlabeled to labeled anti-antibody may be 2:1 to 4:1, and for a different antibody the preferred ratio may be 5:1 to 10:1. The amounts of labeled and unlabeled antibody can be easily adjusted so that the appropriate level of signal is obtained and the total amounts of anti-mouse and anti-sheep antibodies are in excess concentrations. This is as opposed to the customary procedure for preparing a secondary antibody reagent, where the labeling process itself would be optimized to yield the desired level of labeled secondary antibody. After a suitable incubation period, the mixture of liquid and microparticles is placed under the influence of a magnetic field, causing the microparticles to adhere to the walls of the reaction vessel, and the liquid phase is removed. The microparticles, still adhering to the vessel wall, are then washed to remove any remaining unbound analyte and label, and resuspended in a carrier liquid for introduction into a flow cytometer where the microparticles are assayed by flow cytometry for the presence and optionally semi-quantitatively for the amount of the drugs in question. By "semi-quantitatively" we mean that a determination of concentration may be made in relation to the calibrators used for the assay. In many cases, such as an assay for opiates, the assay is designed to detect two or more drugs within a group (e.g. codeine, morphine and hydrocodone), and to give semi-quantitative results relative to, for example, known levels of morphine in calibrator samples. Since the antibody used typically does not cross-react equally with all detected drugs, and because the test cannot determine exactly which opiate drugs are present, the concentration reported relative to the morphine calibrators is only an estimate of opiate drug concentration, not a truly quantitative determination. A suitable apparatus for such analysis is the BioPlex® 2200 analyzer, available from Bio-Rad, Inc. (Hercules, Calif.).

Body fluids that may be analyzed using the invention include both human and other mammalian body fluids, for example, fluids from dogs, cats, cattle, horses, pigs, camels, and other pets or domesticated mammals or zoo mammals. Body fluids from non-mammalian vertebrate animals may also be analyzed using this invention. Body fluids that can be analyzed include blood, serum, plasma, urine, sweat, saliva, and stool samples. The test can be carried out for any necessary purpose, including for law-enforcement purposes, regulatory purposes, sports and/or gambling test purposes, health reasons, hospitalization needs, autopsy procedures, and the like.

The microparticles used in the methods of this invention are described, for example, in U.S. Pat. No. 6,280,618 of Michael Watkins et al., which is hereby incorporated herein in its entirety. That patent also describes how the particles may be used in conducting assays in general.

The assay according to this invention can be carried out using microparticles that either are or are not magnetically responsive. Preferably, however, in these processes the microparticles are composed of a material that is magnetically responsive. The term "magnetically responsive material" is used herein to denote a material that responds to a magnetic field. Magnetically responsive materials of interest in this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, CoO, NiO, $Mn_2O_3$, $Cr_2O_3$, and CoMnP.

Rather than constituting the entire microparticle, the magnetically responsive material is preferably only one component of the microparticle. The remainder consists of a polymeric material to which the magnetically responsive material is affixed and which is chemically derivatized to permit attachment of an assay reagent. The magnetic particles have sizes that are microscopic (and hence termed "microparticles") and that are classifiable into groups according to distinguishable characteristics or differentiation parameters. As described below, the groups are substantially discrete (i.e., non-overlapping), with the mean values of the distinguishing characteristics of adjacent groups sufficiently far apart to permit differentiation of each group from the others by conventional automated detection methods, especially flow cytometry. An assay reagent is bonded to each particle, with substantially all particles within each group bearing the same assay reagent and with different assay reagents from one group to the next. The groups are thus distinguishable not only by their distinctive differentiation parameters for purposes of differentiation but also by the assay reagents bonded to the particles, such that all particles in each group take part in a distinct binding assay, and do so in a selective manner relative to the assay reagents bonded to particles in other groups.

This aspect of the invention further resides in a combination of solid particles for use in the multiplex assay described in the preceding paragraph, the particles being of magnetically responsive material and having a particular detectable parameter that encompasses a range of values that differentiate the particles into two or more substantially discrete groups that are distinguishable by automated detection methods that are appropriate for the particular parameter. The particles bear assay reagents bonded to their surfaces, with a distinct assay reagent for each group.

The magnetic character of the particles permits the automated separation of solid phase from liquid phase at a point in the sequence of the assay prior to the stage at which the particle groups are differentiated according to the differentiation parameter. The separation can serve any of a variety of purposes, including the removal of sample debris from the assay components, the removal of sample components that would otherwise contribute significantly to the background noise at the detection stage, the removal of competing binding members that are not the subject of any of the assays but would otherwise interfere with the results, and the removal of bound from unbound species such as labels, analytes, analyte binding members, and label-binding member conjugates. The particular function in any given assay or combination of assays will depend on the nature of the assay and the assay protocol.

In aspects and embodiments of this invention that involve the use of solid magnetic microparticles, the quantity of magnetically responsive material in the microparticle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. Furthermore, an excessive quantity of magnetically responsive material in the microparticles will produce autofluorescence at a level high enough to interfere with the assay results. It is therefore preferred that the concentration of magnetically responsive material be low enough to minimize any autofluorescence emanating from the material. With these considerations in mind, the magnetically responsive material in a microparticle in accordance with this invention preferably ranges from about 1% to about 75% by weight of the particle as a whole. A more preferred weight percent range is from about 2% to about 50%, a still more preferred weight percent range is from about 3% to about 25%, and an even more preferred weight percent range is from about 5% to about 15%. The magnetically responsive material can be dispersed throughout the polymer, applied as a coating on the polymer surface or as one of two or more coatings on the surface, or incorporated or affixed in any other manner that secures the material in the polymer matrix.

The microparticles can be formed from any material, typically a polymer, that is suitable for producing such microparticles and that bears certain other characteristics that make it useful in these assays. One such characteristic is that the matrix be inert to the components of the biological sample and to the assay reagents other than the assay reagent that is affixed to the microparticle. Other characteristics are that the matrix have minimal autofluorescence, that it be solid and insoluble in the sample and in any other solvents or carriers used in the assay, and that it be capable of affixing an assay reagent to the microparticle. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle.

Functional groups for attachment of the assay reagent can be incorporated into the polymer structure by conventional means, including the use of monomers that contain the functional groups, either as the sole monomer or as a co-monomer. Examples of suitable functional groups are amine groups ($-NH_2$), ammonium groups ($-NH^{3+}$ or $-NR^{3+}$), hydroxyl groups ($-OH$), carboxylic acid groups ($-COOH$), and isocyanate groups ($-NCO$). Useful monomers for introducing carboxylic acid groups into polyolefins, for example, are acrylic acid and methacrylic acid.

Attachment of the assay reagent to the solid phase surface can be achieved by electrostatic attraction, specific affinity interaction, hydrophobic interaction, or covalent bonding. Covalent bonding is preferred. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Examples of suitable useful linking groups are polylysine, polyaspartic acid, polyglutamic acid and polyarginine. In the microparticles for use in the present invention, the preferred linkers are proteins, and particularly bovine serum albumin (BSA).

When the detection of drugs is performed by flow cytometry, care should be taken to avoid the use of particles that emit high autofluorescence since this renders them unsuitable for flow cytometry. Particles created by standard emulsion polymerization techniques from a wide variety of starting monomers generally exhibit low autofluorescence. Conversely, particles that have been modified to increase porosity and therefore surface area (such particles are referred to in the literature as "macroporous" particles) exhibit high autofluorescence. Autofluorescence in such particles further increases with increasing size and increasing percentage of divinylbenzene monomer.

The size range of the microparticles can vary and particular size ranges are not critical to the invention. In most cases, the aggregated size range of the microparticles lies within the range of from about 0.3 micrometers to about 100 micrometers in particle diameter, and preferably within the range of from about 0.5 micrometers to about 40 micrometers. Size may be used as a differentiation parameter among different groups of microparticles; however, for use in this invention the microparticles are preferably all the same size (within tolerances).

Another example of a differentiation parameter that can be used to distinguish among the various groups of particles is fluorescence. Differentiation is accomplished by incorporating various fluorescent materials in the particles, the various fluorescent materials having different fluorescent emission spectra and being distinguishable on this basis.

Fluorescence can in fact be used both as a means of distinguishing the groups from each other and as a means of detection for the assay performed on the particle. The use of fluorescent materials with different emission spectra can be used as a means of distinguishing the groups from each other and as a means of distinguishing the group classification from the assay detections. An example of a fluorescence substance that can be used as a means of distinguishing groups is fluorescein and an example of a substance that can be used for the assay detection is phycoerythrin. Different particle groups are dyed with differing concentrations of fluorescein and assay-specific reporters are labeled with phycoerythrin.

A preferred differentiation parameter for us in the microparticles and processes of this invention is the ratio of two fluorescent substances. In this embodiment all particles are dyed with the same combination of two [or three?] fluorescent dyes and are differentiated into subgroups by differing ratios of the dyes, each subgroup having a distinguishably different ratio.

In one embodiment, the microparticles will have two or more fluorochromes incorporated within them so that each microparticle in the array will have at least three distinguishable parameters associated with it, i.e., side scatter together with fluorescent emissions at two separate wavelengths. For example, the microparticle can be made to contain a red fluorochrome such as Cy5 together with an orange fluorochrome such as Cy5.5. Additional fluorochromes can be used to further expand the system. Each microparticle can thus contain a plurality of fluorescent dyes at varying wavelengths.

Still other examples of a differentiation parameter that can be used to distinguish among the various groups of particles are light scatter, light emission, or combinations of light scatter and emission. Side angle light scatter varies with particle size, granularity, absorbance and surface roughness, while forward angle light scatter is mainly affected by size and refractive index. Thus, varying any of these qualities can serve as a means of distinguishing the various groups. Light emission can be varied by incorporating fluorescent materials in the microparticles and using fluorescent materials that have different fluorescence intensities or that emit fluorescence at different wavelengths, or by varying the amount of fluorescent material incorporated. By using a plurality of fluorescent emissions at various wavelengths, the wavelength difference can be used to distinguish the particle groups from each other and also to distinguish the labels indicating the occurrence of binding reactions in the assay from the labels that identify the particle groups.

Still another example of a differentiation parameter that can be used to distinguish among the various groups of particles is absorbance. When light is applied to microparticles the absorbance of the light by the particles is indicated mostly by the strength of the laterally (side-angle) scattered light while the strength of the forward-scattered light is relatively unaffected. Consequently, the difference in absorbance between various colored dyes associated with the microparticles is determined by observing differences in the strength of the laterally scattered light.

A still further example of a differentiation parameter that can be used to distinguish among the various groups of particles is the number of particles in each group. The number of particles of each group in an assay is varied in a known way, and the count of particles having various assay responses is determined. The various responses are associated with a particular assay by the number of particles having each response.

As the above examples illustrate, a wide array of parameters or characteristics can be used as differentiation parameters to distinguish the microparticles of one group from those of another. The differentiation parameters may arise from particle size, from particle composition, from particle physical characteristics that affect light scattering, from excitable fluorescent dyes or colored dyes that impart different emission spectra and/or scattering characteristics to the microparticles, or from different concentrations of one or more fluorescent dyes. When the distinguishable microparticle parameter is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA), Luminex Corporation Austin. Tex., USA) and Molecular Probes, Inc. (Eugene, Oreg., USA).

A given sample to be assayed may contain drugs or it may contain metabolites or drugs, or it may contain both, and the methods and kits of the invention can determine the presence and, semi-quantitatively, the amount, of either or both. Therefore, for the purpose of describing the invention, the use of the term "drugs" herein is mean to include such drugs, their metabolites, or both.

Drugs whose presence and quantity can be determined using the invention include both the drugs themselves as well as their metabolites, and include, for instance, natural and synthetic opiates such as morphine, heroin, codeine, oxycodone, hydrocodone, propoxyphene, and buprenorphine; amphetamine; methamphetamine, 3,4-methylenedioxy methamphetamine (MDMA or Ecstasy); $\Delta^9$-tetrahydrocannabinol (THC) and related drugs; cocaine (methylbenzoylecgonine, cocaine metabolite) and related drugs; benzodiazepines such as lorazepam, flurazepam, oxazepam and others; barbiturates such as phenobarbital, secobarbital, cyclobarbital and others; methadone and related drugs; phenylcyclidine (PCP, Angel Dust) and related compounds such as PCE, PCPy, TCM, TCP and TCPy, and tricyclic antidepressants (TDA) such as chlorpromazine, clomipramine, doxepin, nortriptylene, amitriptylene and others, and metabolites of the foregoing. In a preferred embodiment the method and kit include drugs falling within all of these classes. Steroids or hormones, or their metabolites, can also be included in the assays of this invention. Creatinine can also be determined to ensure validity of the specimen. A given assay may include two or more of the above drugs, depending on the purpose and expectations. In one embodiment the assay comprises an amphetamine screen which can give a single combined result based on assays for amphetamine and methamphetamine assays, or each assay can be reported separately.

The following represent examples of the invention. However, these are presented only as examples, and are not intended to limit, in any way, the scope of this invention.

EXAMPLES

Example 1

This example illustrates the screening of antibodies and drug-protein conjugates for cross-talk. Several sets of magnetic microparticles, each set dyed in a manner that it can be identified by the BioPlex® 2200 instrument, were each coated with one of several drug-protein conjugates. The conjugates were purchased from East Coast Biologicals (North Berwick, Me.), Biostride Inc (Redwood City, Calif.), Pyxis Laboratories (Lake Forest, Calif.), Arista Biologicals, Allentown, Pa.), Fitzgerald Industries International (Concord, Mass.), and BiosPacific Corp (Emeryville, Calif.). Methods for producing these coated microparticles are described in U.S. Pat. No. 6,280,618. The sets of microparticles were mixed together and suspended in a buffered solution. Antibodies to be tested obtained from MaxMed Laboratories (San Diego, Calif.), Biostride Inc (Redwood City, Calif.) and Pyxis Laboratories (Lake Forest, Calif.) were prepared as separate solutions of 50 μg/mL in a buffer. The assay was performed as follows:

1. 100 μL of microparticle suspension, 50 μL of buffer, and 5 μL of test antibody were combined in a reaction vessel and incubated for 400 seconds at 35° C.
2. A magnetic field was applied to the reaction vessel, the supernatant fluid was aspirated and the particles are washed.
3. 50 μL of anti-IgG antibody-phycoerythrin conjugate was added and the reaction was incubated for 180 seconds at 35° C.
4. The particles were washed as described in step 2 and suspended in 50 μL of buffer.
5. The suspended particles were analyzed by the BioPlex 2200 instrument and fluorescence of phycoerythrin associated with each microparticle set was determined.

Table 1 shows an example of results of testing five different amphetamine antibodies for cross-talk. Each line in Table 1 shows results of one amphetamine antibody to each of fifteen sets of microparticles in the suspension. All of the antibodies used have similar binding to microparticles coated with amphetamine-BSA conjugate #3. Ab 133, however, is unacceptable for use in this assay because it shows significant cross-talk with many non-target microparticles including microparticles coated with conjugates 5, 27, 30, 10, 37, 43, 19, and 50.

Ab 121 recognizes both AMP microparticles (conjugates 3 and 72), but gives more binding to conjugate 3, indicating that it is a better choice. Ab 121 gives low binding to Methamphetamine (MAMP) conjugate 5, but has cross talk with MAMP conjugate 27 which is not acceptable for these assays. PCP conjugate 47 is also unacceptable since all amphetamine antibodies bind it (cross-talk), but conjugate 19 is acceptable for most amphetamine antibodies except Ab 133 and Ab 134. The preferred specification is that it be below 5% of the signal obtained from the target microparticle. For Ab 121, this would be 5% of 14149.

TABLE 1

Evaluation of Five Amphetamine Antibodies for Recognition of Bead Candidates
Excerpted from Q:\BP Tox\BP2200 instrument data files\Cross talk

| conjugate ID → | 3 | 72 | 5 | 27 | 30 | 31 | 10 | 37 |
|---|---|---|---|---|---|---|---|---|
| Conjugate → | AMP-BSA | AMP-BSA | MAMP-BSA | MAMP-BSA | THC-BSA | THC-BSA | BE-BSA | MOR-BSA |
| Antibody ID | | | | | | | | |
| Ab119 | 14797 | 10059 | 130 | 5523 | 51 | 68 | 122 | 21 |
| Ab120 | 14272 | 10605 | 1760 | 11121 | 37 | 14 | 55 | 16 |
| Ab121 | 14149 | 7264 | 13 | 9352 | 36 | 13 | 41 | 15 |
| Ab133 | 15801 | 14589 | 4463 | 16113 | 1344 | 130 | 1684 | 1208 |
| Ab134 | 15421 | 12865 | 245 | 13051 | 195 | 179 | 339 | 315 |

| conjugate ID → | 41 | 43 | 19 | 47 | 48 | 50 | 54 |
|---|---|---|---|---|---|---|---|
| Conjugate → | Barb-BSA | Benz-BSA | PCP-BSA | PCP-BSA | TCA-BSA | Methadone-BSA | MDMA-BSA |
| Antibody ID | | | | | | | |
| Ab119 | 17 | 18 | 36 | 4495 | 42 | 25 | 28 |
| Ab120 | 17 | 19 | 29 | 4366 | 41 | 25 | 25 |
| Ab121 | 17 | 19 | 29 | 3830 | 42 | 25 | 25 |
| Ab133 | 182 | 783 | 2453 | 6346 | 523 | 1246 | 701 |
| Ab134 | 35 | 93 | 198 | 3949 | 90 | 107 | 65 |

Example 2

This example illustrates the covalent attachment of affinity purified donkey anti-sheep IgG antibody to B-phycoerythrin (PE). The PE (part number 100301) was purchased from Cyanotech Corporation, Kailua-Kona, Hi., USA. The anti-sheep antibody was purchased from Lampire Biological Labs, Pipersville, Pa., USA.

The PE was dialyzed against 50 mM $PO_4$, 150 mM NaCl, 5 mM EDTA pH 7.4 (PBS/EDTA) to remove ammonium sulfate and then diluted to 8.0 mg/ml. Succinimidyl-4-(N-maleimidomethyl)cyclohexane-1-carboxylate (SMCC) at 10 mg/ml in dimethylsulfoxide (DMSO) was added to the PE at a molar reaction ratio of 10:1 and incubated at 22±2° C. for 30±5 minutes. The PE-SMCC solution was purified on a Sephadex® G-25 column at ambient temperature using PBS/EDTA buffer and the protein concentration of the PE-SMCC peak was determined at 545 NM. The PE-SMCC was diluted to 2.2 mg/ml and stored at 2-8° C. The antibody was dialyzed into PBS/EDTA and adjusted to a concentration of 5.0 mg/ml. N-succinimidyl-5-acetylthioacetate (SATA) was dissolved in dimethylsulfoxide (DMSO) at a concentration of 10 mg/ml and added to the antibody at a molar reaction ratio of 15:1 and incubated at 22±2° C. for 60±5 minutes. A 10% volume of 0.5 M hydroxylamine, pH 7.0 was added to the antibody-SATA solution and incubated at 22±2° C. for 30±5 minutes. The thiolated antibody solution was purified on a Sephadex G-25 column at ambient temperature using PBS/EDTA buffer and the protein concentration of the thiolated antibody peak was measured at 280 NM. The antibody was diluted to 2.0 mg/ml. The thiolated antibody and PE-SMCC solutions were combined at a molar reaction ratio of 3:1 and incubated at 22±2° C. for 120±15 minutes. N-ethylmaleimide (NEM) in DMSO was added to the reaction at a final concentration of 0.1 mg/ml and incubated at 22±2° C. for 30±5 minutes. The reaction solution was purified on a Sephacryl® S-300 column using 50 mM $PO_4$, 150 mM NaCl, 0.1% sodium azide pH 7.4 and the Ab-PE peak was collected and bovine serum albumin (BSA) was added to a final concentration of 1%. The conjugate solution was filtered thru a 0.2 u filter and the solution stored at 2-8° C.

Example 3

This example illustrates how drug antibodies are selected for cross-reactivity and formulated for use in the assay. Test antibodies are used at varying dilutions in the assay described in Example 4 below to determine the dilution that produces an appropriate dose-response curve based on a series of calibrators containing purified drugs of known concentrations. The calibrators include levels that are above and below the cutoff value for each drug assay. The cutoff value is the concentration, often reported as ng/mL, at or above which a specimen is considered to be positive and below which a specimen is considered to be negative for the drug, drug metabolite, or family of drugs in question. Cross-reactivity is the concentration of the cutoff level divided by the minimum concentration of cross-reactant that will give a positive result. The value is often expressed as percent cross-reactivity. Antibodies that do not cross-react sufficiently with the desired related drugs within a drug family, such as opiates, are rejected. Antibodies that cross-react to an unacceptable degree with benign compounds are also rejected.

After all drugs for the multiplex assay have been identified, they are formulated in a single solution with each antibody at its optimal concentration.

Example 4

This example illustrates how the multiplex assay is performed.

1. 5 µL of specimen of unknown concentration, or calibrator of known concentration; 45 µL of buffer; 100 µL of microparticle suspension prepared as in Example 1 and 50 µL of drug antibody prepared as in Example 1 are combined in a reaction vessel and incubated for 400 seconds at 35° C.
2. A magnetic field is applied to the reaction vessel, the supernatant fluid is aspirated and the particles are washed.
3. 50 µL of anti-IgG antibody-phycoerythrin conjugate is added and the reaction is incubated for 180 seconds at 35° C.
4. The particles are washed as described in step 2, and suspended in 50 µL of buffer.
5. The suspended particles are analyzed by the BioPlex 2200 instrument and fluorescence of phycoerythrin associated with each microparticle set is determined.
6. A calibration curve is constructed by plotting the fluorescent signal generated in response to the calibrators against the known concentration of the calibrators. Examples of the calibration curves are shown in FIGS. 1-4.
7. Semi-quantitative values for drug concentrations are derived for each specimen by calculating the level of drug from the calibration curve that corresponds with the fluorescent signal obtained for the specimen relative to the drug in question.
8. The specimen is interpreted as Positive or Negative by comparing the semi-quantitative level of drug to the cutoff value.

Example 5

This example illustrates results for human urine specimens obtained using the claimed test and results from other methods A multiplex assay was performed using the procedure of Example 4 to test a series of 208 samples that had been screened by commercially available simplex immunoassays and found to be negative for amphetamines, opiates, PCP, benzodiazepines, THC, and cocaine. These specimens were also negative in the multiplex assay.

Specimens positive by a GC/MS method for THC, cocaine, amphetamines, barbiturates, PCP, methadone, or MDMA were also tested using the multiplex assay, and results are shown in Table 2 below. There was close agreement of drug concentrations and interpretation of specimens being positive relative to the suggested cutoff values. (The result for specimen B0707 appears to be a false positive.)

TABLE 2

Comparison of multiplex and GC/MS results

| ID | MultiPlex (ng/mL) | GC/MS (ng/mL) | ID | MultiPlex (ng/mL) | GC/MS (ng/mL) |
|---|---|---|---|---|---|
| THC. Cutoff = 50 ng/mL | | | Cocaine. Cutoff = 50 ng/mL(150) | | |
| BP0551 | 92 | 181 | BP0602 | >600 | 57647 |
| BP0552 | 106 | 132 | BP0603 | 2037 | 1191 |
| BP0553 | 45 | 44 | BP0604 | 269 | 180 |
| BP0554 | 83 | 52 | BP0605 | 285 | 220 |
| BP0555 | 29 | 23 | BP0606 | 279 | 523 |

TABLE 2-continued

Comparison of multiplex and GC/MS results

| ID | MultiPlex (ng/mL) | GC/MS (ng/mL) | ID | MultiPlex (ng/mL) | GC/MS (ng/mL) |
|---|---|---|---|---|---|
| BP0556 | 252 | 1014 | BP0607 | 430 | 255 |
| BP0557 | 40 | 33 | BP0608 | 279 | 314 |
| BP0558 | 138 | 170 | BP0609 | 264 | 310 |
| BP0559 | 167 | 111 | BP0610 | 267 | 19211 |
| BP0560 | 95 | 87 | BP0611 | >600 | 16728 |
| BP0561 | 102 | 90 | BP0612 | 595 | 614 |
| BP0562 | 235 | 437 | BP0613 | 555 | 567 |
| BP0563 | 63 | 66 | BP0614 | 168 | 494 |
| BP0564 | 70 | 65 | BP0615 | 302 | 466 |
| BP0565 | 107 | 85 | BP0617 | 768 | 515 |
| AMP/MAMP. Cutoff 500 or 1000 ng/mL | | | Barbiturates. Cutoff 200 or 300 ng/mL | | |
| BP0651 | >2000 | 12033 | BP0701 | 12131 | 2802 |
| BP0652 | 1436 | 1860 | BP0702 | 4984 | 1298 |
| BP0653 | 4230 | 2614 | BP0703 | 615 | 763 |
| BP0654 | 8284 | 5715 | BP0704 | 564 | 5431 |
| BP0655 | 2312 | 3791 | BP0705 | 1769 | 4663 |
| BP0656 | >2000 | 38893 | BP0706 | 2938 | 470 |
| BP0657 | >2000 | 4907 | BP0707 | 0 | 689 |
| BP0658 | 2372 | 4821 | BP0708 | 811 | 740 |
| BP0659 | 2417 | 3082 | BP0709 | 424 | 393 |
| BP0660 | 4794 | 1784 | BP0710 | 1733 | 2008 |
| BP0661 | 1549 | 1566 | BP0711 | 1192 | 1548 |
| BP0662 | 628 | 1171 | BP0712 | 577 | 451 |
| BP0663 | 1276 | 2102 | BP0713 | 1181 | 646 |
| BP0664 | 5879 | 6146 | BP0714 | 1602 | 1603 |
| BP0665 | 5597 | 6321 | BP0715 | 1676 | 1457 |
| PCP. Cutoff 25 ng/mL | | | Opiates. Cutoff 300 ng/mL | | |
| BP0751 | 274 | 344 | BP0776 | >1200 | 9243 |
| BP0752 | 27 | 30 | BP0777 | 376 | 305 |
| BP0753 | 33 | 37 | BP0778 | 498 | 360 |
| BP0754 | 42 | 45 | BP0779 | 1204 | 835 |
| BP0755 | 68 | 78 | BP0780 | 2047 | 974 |
| BP0756 | 76 | 91 | BP0781 | 850 | 304 |
| BP0757 | 33 | 44 | BP0782 | >1200 | 1258 |
| BP0758 | 121 | 90 | BP0783 | >1200 | 26514 |
| BP0759 | 32 | 48 | BP0784 | >1200 | 1366 |
| BP0760 | 16 | 39 | BP0788 | >1200 | 29884 |
| BP0761 | 28 | 29 | BP0789 | >1200 | 21562 |
| BP0762 | 118 | 112 | BP0790 | >1200 | 2615 |
| BP0763 | 35 | 38 | BP0792 | 870 | 516 |
| BP0764 | 25 | 28 | BP0793 | >1200 | 20102 |
| BP0765 | 18 | 30 | BP0794 | 712 | 342 |
| Methadone. Cutoff 300 ng/mL | | | MDMA. Cutoff 500 ng/mL | | |
| BP0823 | 1041 | 108221 | BP1358 | 7219 | 15803 |
| BP0824 | 1071 | 6884 | BP1359 | 7563 | 15825 |
| BP0825 | 1077 | 10035 | BP1360 | 5846 | 7432 |
| BP0826 | 1014 | 5155 | BP1361 | 895 | 992 |
| BP0827 | 1061 | 11021 | BP1362 | 6908 | 10579 |
| BP0828 | 960 | 2708 | BP1363 | 1698 | 1321 |
| BP0829 | 1037 | 3869 | | | |
| BP0830 | 1065 | 11077 | | | |
| BP0831 | 418 | 302 | | | |
| BP0832 | 876 | 2708 | | | |
| BP0833 | 1074 | 8837 | | | |
| BP0834 | 949 | 1614 | | | |
| BP0835 | 685 | 2159 | | | |
| BP0836 | 1010 | 10137 | | | |
| BP0837 | 981 | 2450 | | | |

Example 6

This example illustrates how the multiplex assay is performed with antibody coated on microparticles, biotinylated drug-protein conjugates, and PE-streptavidin label.

Figure 1:
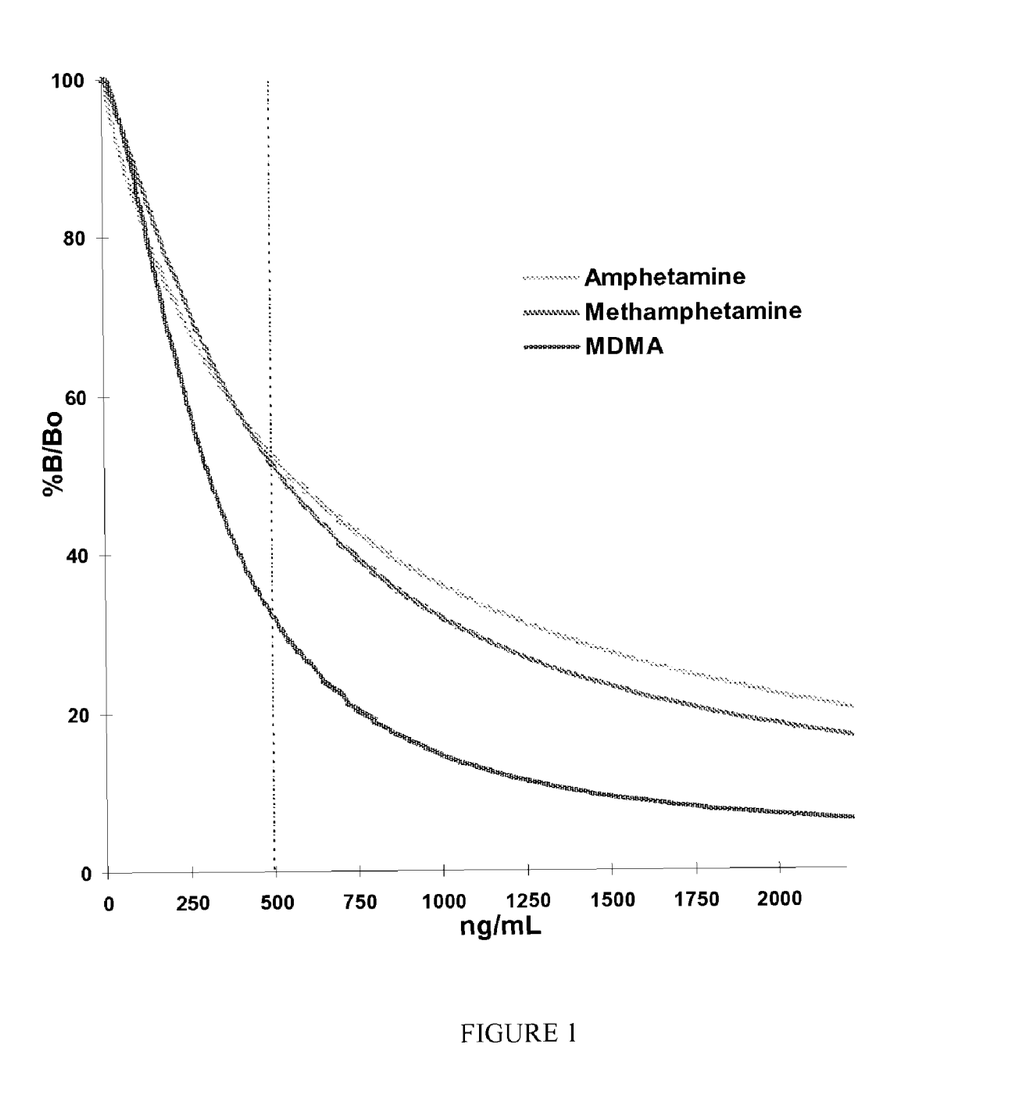
FIG. 1 represents calibration curves for three assays—amphetamine, methamphetamine, and MDMA—in a multiplex consisting of ten assays. Fluorescent signal is normalized by dividing signal for each calibrator by the maximum signal generated in the assay which occurs when no drug is present. The normalized value, % $B/B_0$, is plotted against the concentration of each calibrator (ng/mL).
Figure 2:
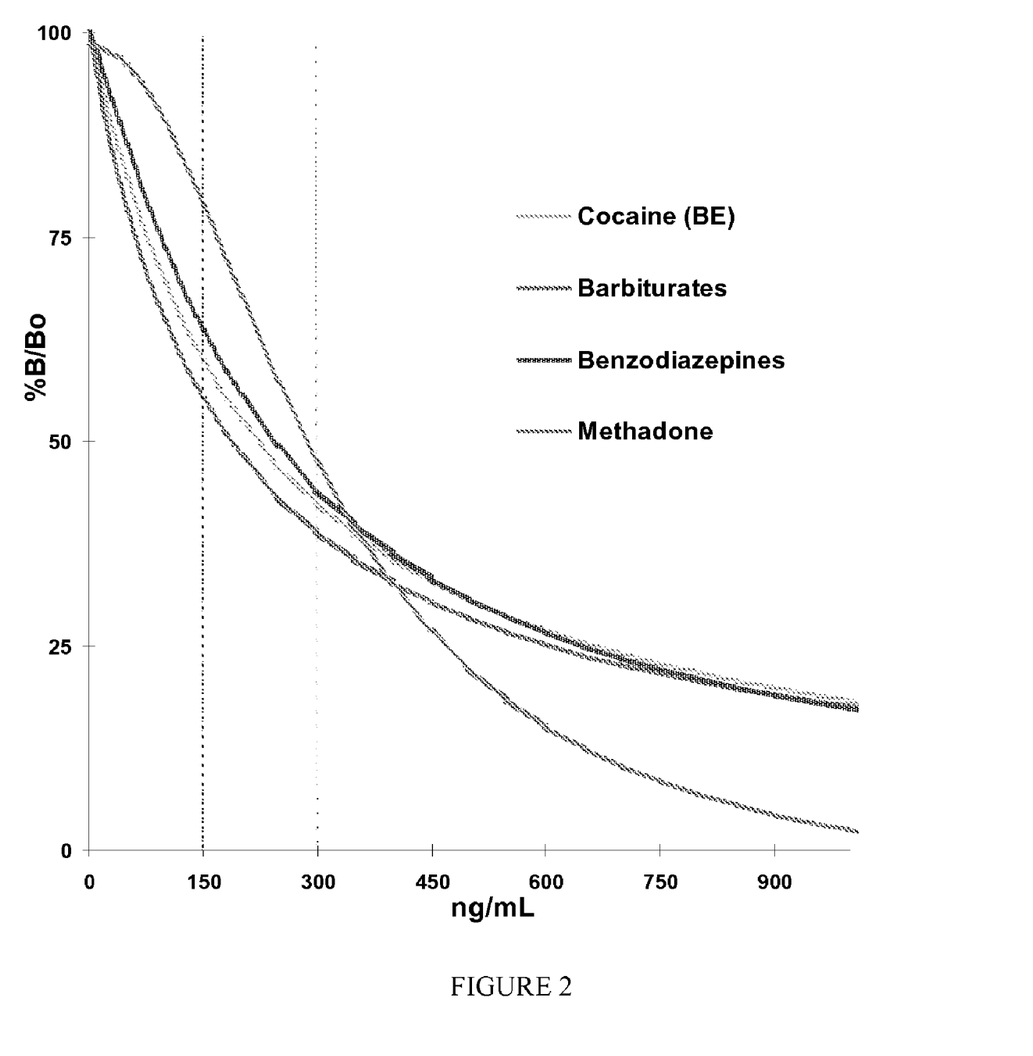
FIG. 2 represents the analogous calibration curves for cocaine metabolite, barbiturates, and methadone.
Figure 3:
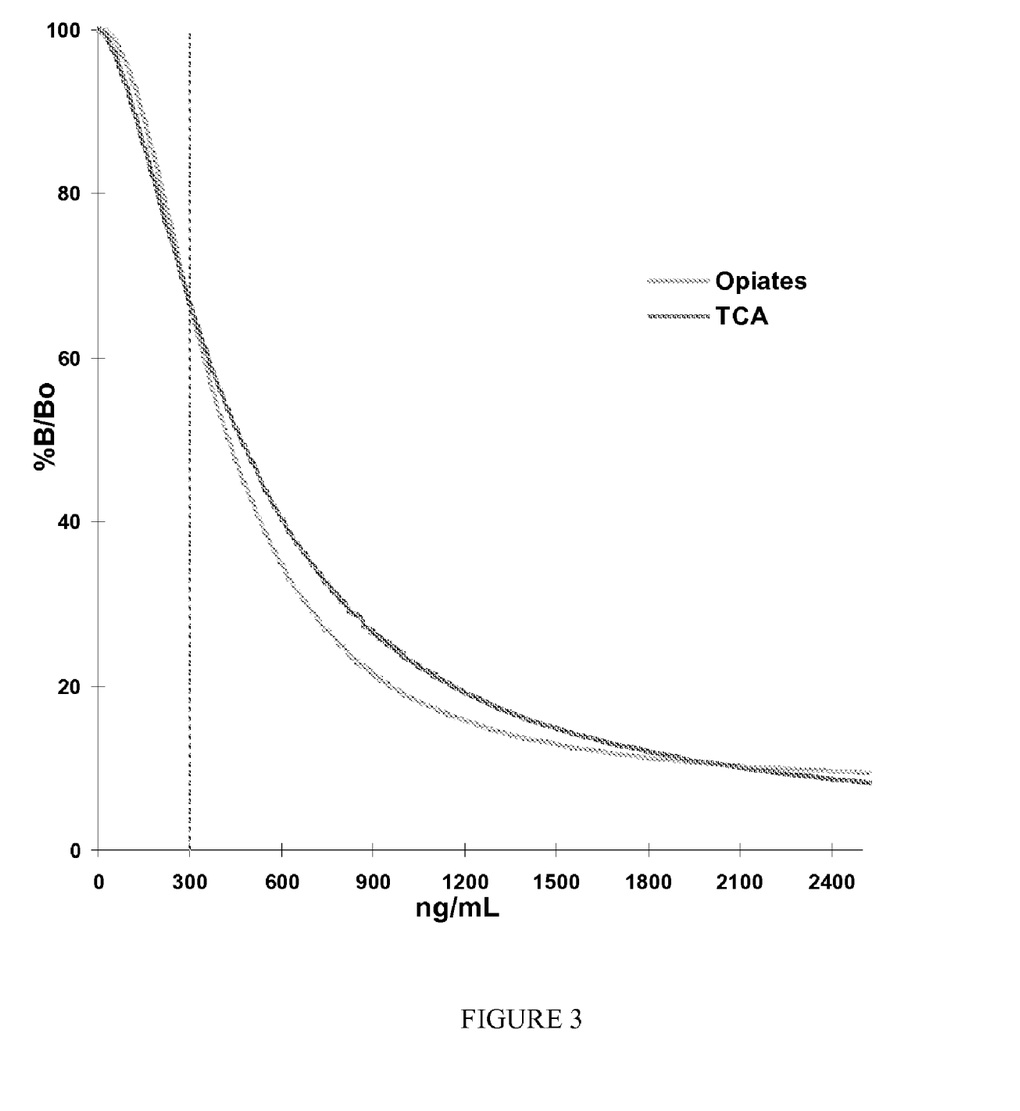
FIG. 3 represents the analogous calibration curves for opiates and tricyclic antidepressants (TCA).
Figure 4:
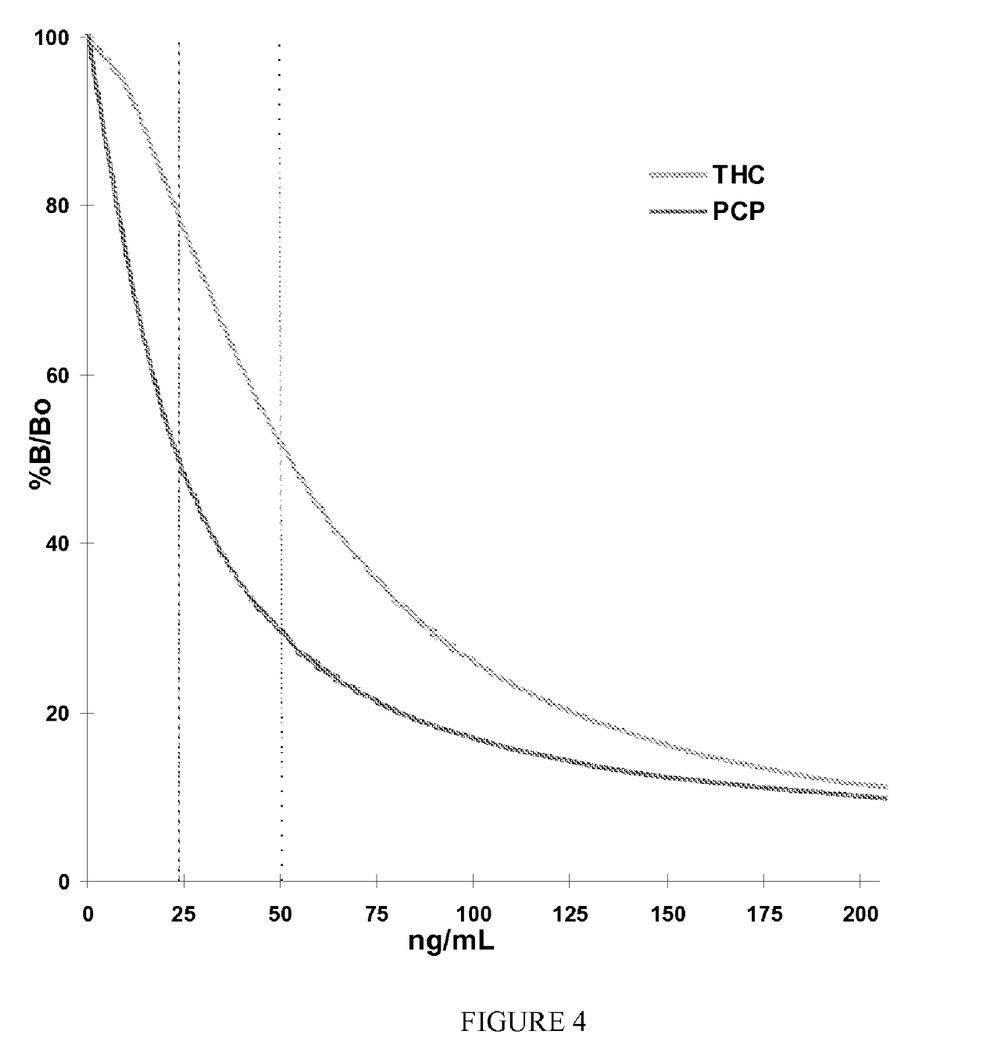
FIG. 4 represents the analogous calibration curves for PCP and THC.
Figure 5:
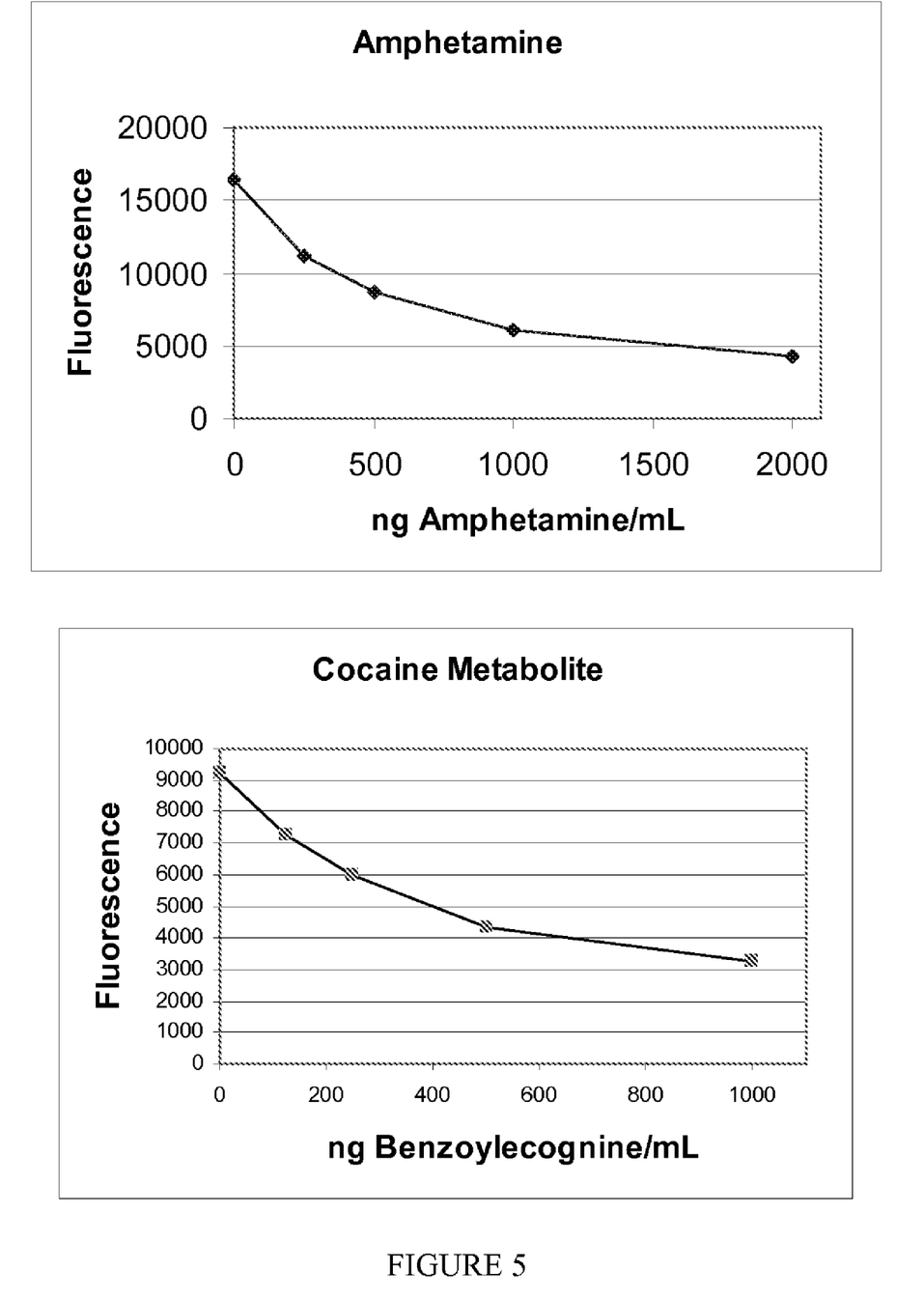
FIG. 5 depicts calibration curves from assays for amphetamine and cocaine metabolite

Biotinylation procedure for Amphetamine-BSA conjugate and Benzoylecognine (cocaine metabolite)-BSA:
Materials:
BE-BSA (East Coast Biologics)
AMP-BSA (Biospecific)
Biotin-LC-NHS (3.25 mg/mL in DMSO)
DMSO
PBS (pH 7.4)
Protocol:
Combine 100 μL BE/BSA or 40 μL AMP BE/BSA (2.86 nM) in PBS in tube.
Add 6 μL DMSO and 4 μL Biotin stock solution in a ten-fold molar ratio—Biotin (28.6 nM):
Drug-BSA (2.86 nM). Incubate 2 hrs at room temperature. The reaction was purified by diafiltration and the final volume adjusted to 400 μL with PBS.
Assay procedure:
1. 50 μL biotinylated drug conjugates prepared as shown above, 5 μL of specimen of unknown concentration, or calibrator of known concentration; and 50 μL of microparticle suspension prepared as in Example 1 are combined in a reaction vessel and incubated for 600 seconds at 35° C.
2. A magnetic field is applied to the reaction vessel, the supernatant fluid is aspirated and the particles are washed.
3. 100 μL of Streptavidin-phycoerythrin conjugate (Jackson ImmunoResearch) are added and the reaction is incubated for 600 seconds at 35° C.
4. The particles are washed as described in step 2, and suspended in 100 μL of buffer.
5. The suspended particles are analyzed by the BioPlex 2200 instrument and fluorescence of phycoerythrin associated with each microparticle set is determined.
6. The resulting calibration curves from the multiplex assay are shown in FIG. 5.

The foregoing descriptions are offered primarily for purposes of illustration. Further modifications, variations and substitutions that still fall within the spirit and scope of the invention will be readily apparent to those skilled in the art. All such modifications coming within the scope of the appended claims are intended to be included therein.

All publications, patents, and patent applications cited herein are hereby incorporated by reference in their entirety for all purposes.

What is claimed is:

1. A method for assaying a sample of a human or mammalian bodily fluid to simultaneously detect the presence in said sample of any of a pre-selected panel of drugs or metabolites of said drugs, said method comprising:
(A) performing a competitive binding assay according to either alternative (i) or alternative (ii), defined as
alternative (i): incubating said sample with (a) subsets of microparticles to which are coupled each of said drugs of said panel and (b) antibodies specific to each of said drugs of said panel with substantially no cross-reactivity to other drugs in said panel, simultaneously in a first common liquid medium,
alternative (ii): incubating said sample with (a) conjugates of each of said drugs of said panel with a label and (b) subsets of microparticles to which are coupled antibodies specific to each of said drugs of said panel with substantially no cross-reactivity to other drugs in said panel, simultaneously in a first common liquid medium,
wherein said microparticles are magnetically responsive and are divided into a plurality of subsets with one subset for each of said drugs of said panel, each subset distinguishable from the other subsets by a differentiation parameter and each subset coupled to either a distinct drug of said panel for alternative (i) or an antibody specific for a distinct drug of said panel for alternative (ii), (B) if alternative (i) is performed, incubating said microparticles with labeled ligands that have binding affinity for said antibodies and recovering said microparticles by magnetic separation from said first liquid medium, and if alternative (ii) is performed, recovering said microparticles by magnetic separation from said first liquid medium without first incubating said microparticles with labeled ligands, (C) suspending said recovered subsets of microparticles in a second liquid medium, and (D) simultaneously analyzing said subsets of microparticles in said second liquid medium by flow cytometry to detect, by way of said label or said labeled ligands, the presence of drugs of said panel in said sample while, by way of said differentiation parameters, differentiating between individual drugs of said panel among those detected.

2. The method of claim 1 wherein step (A) comprises performing said competitive binding assay according to alternative (i).

3. The method of claim 2 wherein each of said drugs is coupled to said microparticles through a member selected from the group consisting of a protein, a nucleotide sequence, a peptide, and an amino acid.

4. The method of claim 2 wherein each of said drugs is coupled to said microparticles through a protein.

5. The method of claim 2 wherein said labeled ligands are labeled anti-IgG antibodies.

6. The method of claim 3 wherein said antibodies are defined as primary antibodies and said labeled ligands are labeled anti-IgG antibodies and an excess of said labeled anti-IgG antibodies relative to said primary antibodies are incubated with said microparticles in step (B).

7. The method of claim 2 wherein said labeled ligands are ligands labeled with phycoerythrin.

8. The method of claim 2 wherein step (A) further comprises incubating said sample with microparticles to which creatinine is coupled and with antibodies specific to creatinine with substantially no cross-reactivity to drugs of said panel, simultaneously with (i) and (ii) in said first common liquid medium, and step (D) further comprises analyzing said microparticles to detect the presence of creatinine in said sample.

9. The method of claim 2 wherein said differentiation parameter is fluorescence and said labeled ligands are ligands labeled with a fluorescent label, the fluorescence of said differentiation parameter and the fluorescence of said labeled ligands having different emission spectra.

10. The method of claim 1 wherein step (A) comprises performing said competitive binding assay according to alternative (ii).

11. The method of claim 10 wherein said label is phycoerythrin.

12. The method of claim 10 wherein step (A) further comprises incubating said sample with a conjugate of creatinine and with microparticles to which are coupled antibodies specific to creatinine with substantially no cross-reactivity to drugs of said panel, simultaneously with (i) and (ii) in said first common liquid medium, and step (D) further comprises analyzing said microparticles to detect the presence of creatinine in said sample.

13. The method of claim 10 wherein said differentiation parameter is fluorescence and said label is a fluorescent label, the fluorescence of said differentiation parameter and the fluorescence of said fluorescent label having different emission spectra 14. The method of claim 1 wherein said panel of drugs consists of a plurality of drugs selected from the group consisting of natural opiates, synthetic opiates, amphetamines, methamphetamine, 3,4-methylenedioxy methamphetamine, $\Delta^9$-tetrahydrocannabinol, cocaine, benzodiazepines, barbiturates, methadone, phenylcyclidine, tricyclic antidepressants, steroids, and hormones.

15. The method of claim 1 wherein said differentiation parameter is fluorescence.

16. The method of claim 15 wherein said differentiation parameter is a ratio of two fluorescent dyes combined with each of said microparticles.

17. The method of claim 1 wherein said bodily fluid is a human bodily fluid.

18. The method of claim 17 wherein said human bodily fluid is a member selected from the group consisting of blood, serum, plasma, urine, saliva, and stool.

* * * * *